United States Patent [19]

Osugi et al.

[11] 4,014,939
[45] Mar. 29, 1977

[54] PROCESS FOR PRODUCING FORMALDEHYDE

[75] Inventors: Minoru Osugi; Takako Endo, both of Niigata, Japan

[73] Assignee: Mitsubishi Gas Chemical Company, Inc., Tokyo, Japan

[22] Filed: June 5, 1975

[21] Appl. No.: 584,366

[30] Foreign Application Priority Data

June 7, 1974 Japan .............................. 49-63984
Dec. 26, 1974 Japan .............................. 50-148390

[52] U.S. Cl. ........................................... 260/603 R
[51] Int. Cl.$^2$ .................. C07C 45/16; C07C 47/04
[58] Field of Search .................. 260/603 R, 603 HF

[56] References Cited

UNITED STATES PATENTS

| | | | |
|---|---|---|---|
| 1,418,448 | 6/1922 | Leggs | 260/603 R |
| 1,555,539 | 9/1925 | Williams | 260/603 R |
| 1,684,634 | 9/1928 | Luther | 260/603 R |
| 1,975,853 | 10/1934 | Lazier | 260/603 R |
| 2,939,883 | 6/1960 | Pundersen | 260/603 R |
| 2,953,602 | 9/1960 | Aries | 260/603 R |
| R21,373 | 2/1940 | Lazier | 260/603 R |

*Primary Examiner*—James O. Thomas, Jr.
*Assistant Examiner*—W. B. Lone

[57] ABSTRACT

Methanol is dehydrogenated at 500°-750° C. using a catalyst whose active components are copper, zinc and sulfur to form a stable product containing 30 to 85% by weight of formaldehyde, 0 to 2% by weight of water, the balance being methanol.

6 Claims, No Drawings

PROCESS FOR PRODUCING FORMALDEHYDE

This invention relates to a process for producing formaldehyde by dehydrogenation of methanol. More particularly, the invention is concerned with a catalyst system used in producing formaldehyde by dehydrogenation of methanol.

For industrial scale production of formaldehyde, methanol is generally subjected to catalytic oxidation dehydrogenation or to catalytic oxidation. According to these processes, formaldehyde is ordinarily obtained as aqueous solutions containing about 40% by weight of formaldehyde. The aqueous solutions, which have heretofore been produced on an industrial scale, have the disadvantage that paraformaldehyde is deposited during storage or may cause clogging of tranportation pipes. In order to prevent the deposition of paraformaldehyde during storage or the clogging of transportation pipes, it has been a common practice in the art that the aqueous formaldehyde solutions are stored or transported at elevated temperatures. When the aqueous formaldehyde solutions are heated, however, side reactions of formaldehyde take place to form formic acid, with the result that the formaldehyde is undesirably degraded in quality. To prevent deposition of paraformaldehyde in aqueous formaldehyde solutions, there has been proposed a process in whih various stabilizers are added to the solutions. This process, however, merely delays the initiation of the deposition of paraformaldehyde, and is not a radical solution to the problem. In fact, the said prior art process is hardly effective for stabilization of aqueous formaldehyde solutions higher of concentration. Further, the paraformaldehyde which is usually obtained by concentrating an aqueous formaldehyde solution is undesirably lowered in solubility when it is used several days after preparation, although it is favorably soluble in water or alcohols when it is used immediately after preparation.

On the other hand, many processes have heretofore been proposed for the production of formaldehyde according to the so-called methanol dehydrogenation. For example, there have been proposed a process using a catalyst composed of copper, silver and silicon (cf. U.S. Pat. No. 2,939,883); a process using a catalyst prepared by adhering zinc metal onto the surface of copper metal (Japanese Patent Publication No. 11853/66); a process using molten zinc, gallium, indium or aluminum, or an alloy thereof (Japanese Patent Publication No. 19251/72); and a process in which methanol is brought into contact with carbon-containing molten zinc or zinc-containing alloy (Japenese Patent Laying-Open-to-Public No. 97808/73). Even such processes, however, cannot yet be said to be satisfactory for industrial scale production.

With an aim to solve the above-mentioned various problems, we have conducted extensive studies to accomplish the present invention.

In the general aspect of the present invention, formaldehyde is produced by dehydrogenation of methanol in the presence of copper, zinc, and sulfur as catalyst components.

In accordance with one embodiment of the invention, there is provided a process of producing formaldehyde by dehydrogenation of methanol in the presence of a catalyst comprising copper, zinc and sulfur.

The catalyst used in the present invention is composed of copper, zinc and sulfur, and the atomic ratio of copper : zinc : sulfur is 1 : 0.001–0.1 : 0.001–0.3, preferably 1 : 0.02–0.1 : 0.05–0.3. The catalyst is not particularly restricted to any one preparation method, and may be prepared according to the precipitation method, thermal decomposition method or adhesion drying method, which is properly selected according to the kinds of starting materials used.

The catalyst used in the present invention is not only high in methanol conversion and gives formaldehyde in a high yield, but also is so active as to be continuously usable over a period of more than 10 hours. If either one of zinc and sulfur is eliminated from the catalyst composition of the present invention, no such high conversion and yield as in the present invention can be obtained with such a high activity as mentioned above.

The materials constituting the catalyst used in the present invention may be in any form regardless of whether they are powdery or granular. Examples of the copper source are copper metal, copper nitrate, copper sulfate, copper hydroxide and copper oxide, and examples of the zinc and sulfur sources are zinc nitrate, zinc sulfate, zinc sulfide and ammonium sulfate.

The reaction temperature adopted in the present invention is 500° to 750° C., preferably 600° to 700° C., in terms of the catalyst layer temperature. To the catalyst layer, methanol is ordinarily fed in the form of vapor together with hydrogen. The amount of methanol to be fed varies depending on the size and shape of the reactor used, but is preferably 0.2 to 0.5 mole/hr per 20 ml. of the catalyst.

In a specific and preferred embodiment of the invention, sulfur may be used in the form of a gaseous compound (e.g. sulfur dioxide, hydrogen sulfide, etc.), as a part of the catalyst or in addition to the catalyst comprising copper, zinc and sulfur. Such gaseous sulfur component may be mixed into the starting gaseous feed or directly into a reaction zone, either continuously or intermittently. The preferred amount of the gaseous sulfur compond is 0.01 – 2% by mole and preferably 0.1 – 1% by mole, based on the feed amount of starting methanol. One advantage of this particular embodiment is the possibility to prevent the catalytic activity of the catalyst system from degradation.

The product obtained by the present process consists of, in general, 30 to 85% by weight of formaldehyde, 0 to 2% by weight of water, and the balance of methanol. Thus, the product is extremely low in water content, and formaldehyde can be obtained in a high yield.

The product obtained according to the present invention has specific properties which are entirely different from those of the aforesaid conventional aqueous formaldehyde solutions and paraformaldehyde. That is, the product of the present invention is a clear solution at normal temperature in case the concentration of formaldehyde in the product is lower than about 70% by weight, and deposits no solids even when allowed to stand as it is at normal temperature for more than 3 months. In case the concentration of formaldehyde is higher than about 70% by weight, the product is a white solid at normal temperature. However, when heat is applied, the solid product easily melts to form a clear solution, which when cooled, again returns to a solid. Even though the said melting by heating and solidification by cooling are repeated, the solid does not change in melting temperatue. In the other words, the product of the invention is characterized by its stability due to the combination of a high formaldehyde concentration of 30% by weight or more with a relatively high concentration of methanol and a low water concentration of 2% by weight or less. For example, a normally solid product comprising 75.1% by weight of formaldehyde, 24.6% by weight of methanol and 0.3% by weight of water, which was obtained according to the present invention, was heated to about 30° C to 35° C. to form a clear solution, which was then cooled to form a solid. The above-mentioned melting and solidification were continued for 30 days once a day, but the solid product did not change in melting temperature. This indicates that the formaldehyde obtained according to the present invention is quite stable. Thus, the product of the present invention is entirely different in properties from the conventional aqueous formaldehyde solutions and paraformaldehyde, the latter being obtained by concentration of the aqueous formaldehyde solutions.

Further, the gas generated during the reaction according to the present invention, is composed mainly of hydrogen, carbon monoxide, methane and carbon dioxide, and hence can be utilized directly as industrial fuel or the like.

The present invention is illustrated in detail below with reference to examples. In the examples, the conversion and the yield were calculated according to the following equations:

Conversion (%) = Reacted methanol (moles)/Fed methanol (moles) × 100

Yield (%) = Formed formaldehyde (moles)/Fed methanol (moles) × 100

EXAMPLE 1

A mixture comprising 50 g. of cupric oxide, 20 g. of ammonium sulfate and 2 g. of zinc oxide was sufficiently pulverized by means of a kneader. thereafter, the pulverized mixture was brought to the form of a paste by addition of 30 ml. of water, and then molded into tablets of 3 mm. in diameter and 3 mm. in thickness. Subsequently, the tablets were subjected to reduction in a hydrogen atmosphere at 200° C. for 30 minutes and then at 600° C. for 30 minutes to prepare a catalyst.

20 Milliliters of the thus prepared catalyst was filled in a quartz glass-made tubular reactor of 21 mm. in inner diameter. Into the reactor, 15 g/hr (0.469 mole) of methanol vapor and an equimolar amount of hydrogen were introduced through one end, and were reacted with each other at a catalyst layer temperature of 650° C. As the result, the conversion was 76.5%, the yield was 61.3%, and the catalyst activity lasted for more than 24 hours. The product was composed of 71.0% by weight of formaldehyde, 1.5% by weight of water and the balance of methanol. Further, the gas generated due to the reaction was composed of 84.5% by weight of hydrogen, 10.4% by weight of carbon monoxide, 4.1% by weight of methane and 1.0% by weight of carbon dioxide.

EXAMPLE 2

242 Grams of copper nitrate trihydrate and 5.8 g. of zinc nitrate hexahydrate were dissolved in 1,500 ml. of water. Into the resulting aqueous nitrate solution, a solution of 82 g. of sodiumhydroxide in 500 ml. of water was gradually dropped over a period of about one hour, whereby precipitates were formed. The precipitates were recovered by filtration, and then suspended in about 1,500 ml. of water, and the resulting suspension was subjected to filtration with vigorous stirring for 15 minutes. This washing operation was repeated 6 times to obtain a cake. This cake was sufficiently mixed by means of a kneader with a solution of 26.2 g. of ammonium sulfate in 50 ml. of water, and the resulting mixture was molded into tablets of 3 mm. in diameter and 3 mm. in thickness. Subsequently, the tablets were subjected to reduction in a hydrogen atmosphere at 200° C. for 30 minutes and then at 600° C. for 30 minutes to prepare a catalyst.

Using the thus prepared catalyst, the same reaction as in Example 1 was effected. As the result, the conversion was 80.3%, the yield was 57.0%, and the catalyst activity lasted for more than 20 hours. Further, the product was composed of 71.8% by weight of formaldehyde, 1.7% by weight of water, and the balance of methanol.

EXAMPLE 3

50 Grams of cupric oxide, 40 g. of anhydrous copper sulfate and 2 g. of zinc oxide were treated in the same manner as in Example 1 to prepare a catalyst. Using this catalyst, the same reaction as in Example 1 was effected. As the result, the conversion was 85.1%, the yield was 57.5%, and the catalyst activity lasted for more than 20 hours. The product was composed of 76.8% by weight of formaldehyde, 2.0% by weight of water, and the balance of methanol.

EXAMPLE 4

To 30 ml. of water were added 100 g. of granular copper of 2 to 3 mm. in diameter, 2 g. of ammonium sulfate and 0.5 g. of zinc oxide. The resulting mixture was sufficiently kneaded, and then freed by evaporation from water by means of a rotary vacuum dryer to form a solid (in such a state that a mixture of ammonium sulfate and zinc oxide had adhered onto the surface of the copper). This solid was subjected to reduction in a hydrogen atmosphere at 200° C. for 30 minutes and then at 600° C. for 30 minutes to prepare a catalyst.

Using the thus prepared catalyst, the same reaction as in Example 1 was effected. As the result, the conversion was 68.9%, the yield was 59.5%, and the catalyst activity lasted for more than 30 hours. The product was composed of 64.1% by weight of formaldehyde, 1.2% by weight of water, and the balance of methanol.

EXAMPLE 5

To 30 ml. of water were added 100 g. of granular copper of 2 to 3 mm. in diameter and 6 g. of anhydrous zinc sulfate. The resulting mixture was sufficiently kneaded, and then freed by evaporation from water by means of a rotary vacuum dryer to form a solid (in such a state that zinc sulfate had adhered onto the surface of the copper). This solid was subjected to the same reduction as in Example 4 to prepare a catalyst.

Using the thus prepared catalyst, the same reaction as in Example 1 was effected. As the result, the conversion was 75.0%, the yield was 61.6%, and the catalyst activity lasted for more than 10 hours. The product was composed of 69.8% by weight of formaldehyde, 1.2% by weight of water, and the balance of methanol.

EXAMPLE 6

To 30 ml. of water were added 100 g. of granular copper of 2 to 3 mm. in diameter and 2 g. of zinc sulfide. The resulting mixture was sufficiently kneaded, and then freed by evaporation from water in the same manner as in Example 4 to form a solid (in such a state that zinc sulfide had adhered onto the surface of the copper). This solid was subjected to the same reduction as in Example 4 to prepare a catalyst.

Using the thus prepared catalyst, the same reaction as in Example 1, except that the catalyst layer temperature was varied to 700° C. was effected. As the result, the conversion was 58.6%, the yield was 51.0%, and the catalyst activity lasted for more than 10 hours. The product was composed of 53.6% by weight of formaldehyde, 0.1% by weight of water, and the balance of methanol. Further, the gas generated due to the reaction was composed of 89.7% by weight of hydrogen, 10.1% by weight of carbon monoxide, 0.1% by weight of methane and 0.1% by weight of carbon dioxide.

COMPARATIVE EXAMPLE 1

A catalyst was prepared in the same manner as in Example 1 by use of 50 g. of cupric oxide, 100 g. of ammonium sulfate and 2 g. of zinc oxide (i.e. the atomic ratio of copper : sulfur = 1 : 0.6). Using the thus prepared catalyst, the same reaction as in Example 1 was effected. As the result, the conversion was 15.3% and the yeild was 11.0%. The results show that the conversion and the yield are greatly lowered with increasing content of sulfur in the catalyst composition.

COMPARATIVE EXAMPLE 2

A catalyst was prepared in the same manner as in Example 1 by use of 50 g. of cupric oxide, 20 g. of ammonium sulfate and 11 g. of zinc oxide (i.e. the atomic ratio of copper : zinc = 1 : 0.22). Using the thus prepared catalyst, the same reaction as in Example 1 was effected. As the result, the conversion was 87.2% and the yield was 16.6%. The results show that with increasing content of zinc in the catalyst composition, side reactions proceed to lower the yield to a great extent.

COMPARATIVE EXAMPLE 3

A copper-zinc catalyst was prepared in the same manner as in Example 1 without using ammonium sulfate. Using the thus prepared catalyst, the same reaction as in Example 1 was effected. As the result, the conversion was 91.7% and the yield was 14.5% and thus was low.

COMPARATIVE EXAMPLE 4

A copper-sulfur catalyst was prepared in the same maner as in Example 1 by use of 50 g. of cupric oxide and 20 g. of ammonium sulfate without using zinc oxide. Using the thus prepared catalyst, the same reaction as in Example 1 was effected. As the results, the conversion was about 70% and the yield was about 60% at the 1st to 2nd hour after initiation of the reaction, but the catalyst activity gradually deteriorated with lapse of time, and the conversion become 42% and the yield became 38% at the 5th hour after initiation of the reaction.

EXAMPLE 7

A mixture comprising 50 g. of cupric oxide and 2 g. of zinc oxide was sufficiently pulverized by means of a kneader. Thereafter, the pulverized mixture was brought to the form of a paste by addition of water, and then molded into tablets of 3 mm. in diameter and 3 mm. in thickness. Subsequently, the tablets were subjected to reduction in a hydrogen atmosphere at 200° C. for 30 minutes and then at 600° C. for 30 minutes to prepare a catalyst.

20 Milliliters of the thus prepared catalyst was filled in a quartz glass-made tubular reactor of 21 mm. in inner diameter. Into the reactor, 15 g/hr (0.469 mole) of methanol vapor, an equimolar amount of hydrogen and 0.18 g/hr of sulfurous acid gas were introduced through one end, and were reacted with each other at a catalyst layer temperature of 650° C. As the result, the conversion was 73.4%, the yield was 61.7%, and the catalyst activity lasted for more than 120 hours. The product was composed of 67.5% by weight of formaldehyde, 1.4% by weight of water, and the balance of methanol.

EXAMPLE 8

In the same manner as in Example 7, a catalyst was prepared by use of 50 g. of cupric oxide and 2 g. of zinc oxide. Using the thus prepared catalyst, the same reaction as in Example 7 was effected, except that the sulfurous acid gas was replaced by 0.096 g/hr of hydrogen sulfide. As the result, the conversion was 69.5%, the yield was 60.2%, and the catalyst activity lasted for more than 70 hours. The product was composed of 64.9% of formaldehyde, 0.8% of water, and the balance of methanol.

EXAMPLE 9

In the same manner as in Example 7, a catalyst was prepared by use of 50 g. of cupric oxide, 20 g. of ammonium sulfate and 2 g. of zinc oxide. Using the thus prepared catalyst, the same reaction as in Example 7 was effected except that the amount of the sulfurous acid gas was varied to 0.06 g/hr. As the result, the conversion was 73.0%, the yield was 62.1%, and the catalyst activity lasted for more than 100 hours. The product was composed of 68.2% by weight of formaldehyde, 1.3% by weight of water, and the balance of methanol.

EXAMPLE 10

242 Grams of copper nitrate trihydrate and 5.8 g. of zinc nitrate hexahydrate were dissolved in 1,500 ml. of water. Into the resulting aqueous nitrate solution, a solution of 8.2 g. of sodium hydroxide in 500 ml. of water was gradually dropped over a period of about one hour, whereby precipitates were formed. The precipitates were recovered by filtration and then suspended in about 1,500 ml. of water, and the resulting suspension was subjected to filtration with vigrous stirring for 15 minutes. This washing operation was repeated 6 times to obtain a cake. The thus obtained cake was molded into tablets of 3 mm in diameter and 3 mm. in thickness. Subsequently, the tablets were subjected to reduction in a hydrogen atmosphere at 200° C. for 30 minutes and then at 600° C. for 30 minutes to prepare a catalyst.

Using the thus prepared catalyst, the same reaction as in Example 7 was effected except that the amount of the sulfurous acid gas was varied to 0.112 g/hr. As the result, the conversion was 73.7%, the yield was 56.8%, and the catalyst activity lasted for more than 90 hours. The product was composed of 66.5% by weight of formaldehyde, 0.7% by weight of water, and the balance of methanol.

EXAMPLE 11

To 30 ml. of water were added 100 g. of granular copper of 2 to 3 mm. in diameter and 0.5 g. of zinc oxide. The resulting mixture was sufficiently kneaded, and then freed by evaporation from water by means of a rotary vacuum dryer to form a solid (in such a state that zinc oxide had adhered onto the surface of the copper). This solid was subjected to reduction in a hydrogen atmosphere at 200° C. for 30 minutes and then at 600° C. for 30 minutes to prepare a catalyst.

Using the thus prepared catalyst, the same reaction as in Example 7 was effected. As the result, the conversion was 71.2%, the yield was 59.7%, and the catalyst activity lasted for more than 130 hours. The product was composed of 65.7% by weight of formaldehyde, 0.8% by weight of water, and the balance of methanol.

EXAMPLE 12

Using the same catalyst as in Example 7, the same reaction as in Example 7 was effected except that 0.024 g/min of the sulfurous acid gas was fed for 20 minutes intermittently at intervals of 2 hours. As the result, the conversion was 79.0%, the yield was 60.8%, and the catalyst activity lasted for more than 120 hours. The product was composed of 72.4% by weight of formaldehyde, 1.9% by weight of water, and the balance of methanol.

COMPARATIVE EXAMPLE 5

A catalyst was prepared in the same manner as in Example 7, except that the zinc oxide was not used. Using the thus prepared catalyst, the same reaction as in Example 7 was effected. As the result, the conversion was about 70% and the yield was about 60% at the 1st to 2nd hour after initiation of the reaction, but the catalyst activity gradually deteriorated with lapse of time, and the conversion became 46% and the yield became 39% at the 10th hour after initiation of the reaction.

EXAMPLE 13

Using the same catalyst and the same reaction condition as in Example 7, the reaction was effected, except that the reaction temperature was changed to 600° C. As a result, the conversion was 44.5%. the yield was 36.2%, and the catalyst activity lasted for more than 120 hours.

The product was composed of 37.9% by weight of formaldehyde, 1.3% by weight of water and the balance of methanol.

What we claim is:

1. A process for the production of formaldehyde which comprises dehydrogenating methanol in the presence of a catalytically effective amount of a catalyst consisting of copper, zinc and sulfur as catalyst components at a temperature of 500° to 750° C. wherein the atomic ratio of said catalyst components is 1:0.001–0.1:0.001–0.3 for Cu:Zn:S.

2. A process as claimed in claim 1, wherein said catalyst components are included together as a solid mass.

3. A process as claimed in claim 1, wherein a part or the whole of the sulfur as one of said catalyst components is provided for the reaction in the form of a gaseous sulfur compound selected from the group consisting of sulfur dioxide, and hydrogen sulfide.

4. A process as claimed in claim 3, wherein the amount of said gaseous sulfur compound is 0.01 – 2% by mole, based on the amount of methanol feed.

5. A process as claimed in claim 1, wherein the reaction temperature is from 600° to 700° C.

6. A process as claimed in claim 1, wherein the methanol feed rate is 0.2 to 0.5 moles/hr. per 20 ml. of the catalyst.

* * * * *